United States Patent [19]

Wolfangel et al.

[11] 4,075,314
[45] Feb. 21, 1978

[54] STANNOUS PYROPHOSPHATE TECHNETIUM-99m COMPOSITIONS

[75] Inventors: Robert G. Wolfangel, Ballwin; Howard A. Anderson, Kirkwood, both of Mo.

[73] Assignee: Mallinckrodt, Inc., St. Louis, Mo.

[21] Appl. No.: 681,626

[22] Filed: Apr. 29, 1976

[51] Int. Cl.$^2$ ..................... A61K 43/00; A61K 29/00
[52] U.S. Cl. ........................................ 424/1; 250/303; 424/9
[58] Field of Search ....................... 250/303; 128/2 A; 424/1, 1.5, 9

[56] References Cited

U.S. PATENT DOCUMENTS

| 3,851,044 | 11/1974 | Adler et al. | 424/1 |
| 3,931,396 | 1/1976 | Bardy et al. | 424/1 |

OTHER PUBLICATIONS

Cohen et al., C. R. Acad. Sc. Paris, 275: 1719–1721–Series D, Oct. 9, 1972.

Hegesippe et al., Journal of Nuclear Biology and Medicine, vol. 17, No. 3, 1973, pp. 93–96.

*Primary Examiner*—Benjamin R. Padgett
*Assistant Examiner*—Christine M. Nucker
*Attorney, Agent, or Firm*—Roy J. Klostermann

[57] ABSTRACT

Improved stannous pyrophosphate technetium-99m compositions.

16 Claims, No Drawings

STANNOUS PYROPHOSPHATE TECHNETIUM-99m COMPOSITIONS

BACKGROUND OF THE INVENTION

This invention relates to the field of radioactive pharmaceuticals and more specifically to improved bone-seeking radionuclide compositions suitable for use in skeletal imaging or bone scanning.

Cohen et al. C. R. Acad. Sc. Paris 275:1719-1721 Series D., Oct. 9, 1972, disclose scintigraphy compositions containing sodium pyrophosphate labeled with technetium 99m. Likewise, U.S. Pat. No. 3,851,044 discloses compositions containing technetium 99m stannous pyrophosphates complexes as well as reducing agents and antioxidants. U.S. Pat. No. 3,931,396 discloses a method for preparing pyrophosphate-tin compositions labeled with technetium 99m.

Typically, these compositions are prepared just prior to patient use by labeling the pyrophosphate with technetium utilizing sodium pertechnetate solution. Kits containing stannous pyrophosphate suitable for labeling are commercially available. The stannous pyrophosphate dissolves in the sodium pertechnetate solution. Simultaneously a chemical reaction occurs between the stannous and pertechnetate ions. This redox chemical reaction is commonly thought to involve oxidation of stannous to stannic, reduction of technetium $^{(+7)}$ to technetium $^{(+3\ -\ +6)}$, followed by binding of the reduced form of technetium to the stannous pyrophosphate complex in some manner.

The efficiency with which technetium is reduced and bound to the pyrophosphate complex determines the purity of the final bone scanning composition as judged by the quality of skeletal images obtained. Where there is failure to completely reduce and bind technetium to the pyrophosphate complex poor quality bone scan images result and are identified by the appearance of objectionably high levels of technetium radioactivity in the muscles and other soft tissues of the body. Often this is caused by oxidizing agents which are introduced as contaminants of the stannous pyrophosphate composition or sodium pertechnetate solution. These oxidizing agents compete with pertechnetate for stannous ions or react with other chemical forms of technetium present to cause regeneration of pertechnetate.

Similarly poor quality images result when unreacted technetium or technetium in other chemical forms are present in the labelled bone scanning compositions. As the quantity of unreacted technetium or regenerated pertechnetate in the bone scanning composition increases a corresponding proportionate decrease in bone scanning quality occurs.

Another frequently but as yet unexplained phenomenon is a trend for technetated stannous pyrophosphates to deposit in the liver in excessive quantities. This liver deposition is unacceptable since skeletal tissue in this region is masked on the scan. This may be caused by the formation of colloidal stannous compounds due to incomplete reaction of the stannous component with the pyrophosphate. Kupffer cells of the liver would then be able to phagocytize the colloidal stannous compounds. Similarly trace chemical impurities present in varying amounts within sodium pertechnetate solutions can cause formation of insoluble or colloidal forms of technetium stannous compounds. Again, these cells could be phagocytized by the Kupffer cells of the liver.

In order to preserve the potency of the unlabelled stannous pyrophosphate compositions during periods of shelf storage the valence of the tin must be preserved in the +2 state. This is generally accomplished by sealing the vial in the absence of oxygen (i.e., under nitrogen). However, such procedures have not completely solved this problem. A second but related problem is caused by the introduction of contaminants during labeling of the stannous pyrophosphate compositions. These contaminants may be atmospheric oxygen, dissolved oxygen organic impurities, di or trivalent cations, etc. The net result of contaminant oxidizing agents is to interfere with the reduction and binding of technetium to the pyrophosphate complex. The other impurities tend to form technetium species which display a propensity to deposit in liver tissues. Consequently the preservation of stannous in the +2 state prior to reconstitution and labeling, prevention of competitive reactions which interfere with pertechnetate reduction, prevention of reoxidation of reduced technetium to pertechnetate and prevention of the formation of technetium compounds which localize in non-osseous tissues, particularly liver tissue, would represent a significant improvement in the overall quality and reliability of technetium bone scanning agents and, therefore, would be an advancement in the art.

SUMMARY OF THE INVENTION

Briefly, the present invention is directed to improved compositions or agents adapted for use in skeletal imaging which comprise divalent tin, pyrophosphate, technetium—99m and ascorbate. The invention is also directed to improved compositions for use in preparing bone scanning agents useful in skeletal imaging which comprise divalent tin, pyrophosphate and ascorbate in sterile, lyophilized form. The invention is further directed to methods for using them in bone scanning or skeletal imaging.

The unlabeled compositions of the instant invention are advantageous in that the (+2) valency of tin in the composition is maintained for extended periods thereby providing a product with a good shelf life. Likewise, after labeling, reoxidation of reduced technetium to pertechnetate and the formation of technetium compounds which localize in non-osseous tissue are reduced or eliminated. Consequently, good quality scans are obtained.

The amount of ascorbate used in the compositions in the practice of this invention is sufficient to reduce or prevent (1) the oxidation of Sn $^{+2}$ to Sn $^{+4}$ during extended storage and (2) reoxidation of reduced technetium and the formation of technetium labeled impurities which localize in non-osseous tissue. Typically this is an amount of from about .1 mg. to 2.5 mg., preferably from about .21 mg. to about 1.2 mg. per mg. of divalent tin. Surprisingly, if the compositions additionally contain perchlorate, it interacts in some manner to reduce reoxidation of reduced technetium and the formation of technetium compounds which localize in non-osseous tissue better than either ascorbate or perchlorate alone over extended periods. Typically, the amount of perchlorate used is from about 4.8 mg. to about 48 mg., preferably 20 mg. to 30 mg. per mg. of divalent tin.

Typically, the molar ratio Sn/$P_2O_7$ is in the range of about 0.010/1.0 to about 0.58/1.0. The ratio $P_2O_7$/Tc-99m is in the range of about 0.012 mg/mCi to about 4 mg/mCi. In the preferred compositions of the invention, the ratio Sn/$P_2O_7$ is in the range of about 0.02/1.0 to about 0.06/1.0 and the ratio $P_2O_7$/Tc-99m is in the range of about 0.03 mg/mCi to about 1.2 mg/mCi.

The tin, pyrophosphate, ascorbate and optionally perchlorate can be prepared in advance in sterile form, lyophilized if desired, ready for extemporaneous constitution of the complete scanning agent by the aseptic addition of pertechnetate solution from a conventional technetium generator.

The compositions of the invention are prepared by the following general method:

A solution containing stannous ions, pyrophosphate ions, ascorbate ions and optionally perchlorate ions in the desired proportions is prepared. The pH is adjusted to the range of about 4 to 8, preferably 5 to 7 and the solution is sterilized by filtration through a membrane filter such as the Millipore 0.22 micron filter supplied by Millipore Corporation, Bedford, Mass. The solution may be lyophilized. To this solution or lyophilized powder is added a solution of pertechnetate ions containing the desired amount of Tc-99m. In the preparation of the compositions, solutions of sodium pyrophosphate and stannous chloride may be mixed, or one of the salts in dry form may be dissolved in a solution of the other. If the composition contains perchlorate it is added to the mixture of sodium pyrophosphate and chloride. This mixture may require acidification to prevent hydrolytic precipitation of basic tin compounds and if so 1N HCl may be used to adjust the pH to 5 to 7. Next ascorbic acid is added to provide the ascorbate.

In lieu of stannous chloride, other pharmaceutically suitable stannous salts such as stannous sulfate may be employed as the source of stannous ions. Similarly, other pharmaceutically acceptable alkalimetal pyrophosphates or ammonium pyrophosphate may be used as the source of pyrophosphate ions. Likewise, in lieu of ascorbic acid, pharmaceutically acceptable ascorbates such as alkalimetal ascorbates may be used as the source of the ascorbate ions. Similarly, other pharmaceutically acceptable perchlorates such as alkalimetal perchlorates may be used as the source of the perchlorate.

Since the stannous pyrophosphate technitium-99m complex of the invention is administered by parenteral injection, it must be sterile. Because of the short half-life of Tc-99m, the compositions of this invention are usually prepared in sterile lyophilized form in advance and the technetium-99m, in the form of a sterile pertechnetate solution, is added shortly before the scanning agent is to be used. Sterile solutions of sodium pertechnetate are widely available as such or are prepared as needed by elution of a technetium-99m generator. This technology is well known.

In toxicity and tissue distribution studies, it was found that the novel bone scanning compositions of the invention are devoid of acute and subacute toxic effects at dosage levels up to 100 times the maximum single dose anticipated in clinical use. The tissue distribution of the compositions of the invention compares favorably to that of other technetium-99m labeled inorganic phosphate polymers but blood clearance and bone uptake appears to be more rapid while uptake by marrow, kidneys and skeletal muscle is apparently less.

Typically, the compositions of this invention are labeled to provide 10 to 250 mCi per vial. Dosage varies from about 0.14 mCi/kg to about 0.36 mCi/kg. Bone scans are carried out using conventional techniques and equipment such as a gamma camera.

The invention will now be illustrated by the following Examples:

EXAMPLE 1

A. Solution Preparation 1,600 ml. of water for injection was added to an appropriate vessel. While stirring continuously, the water for injection was purged with nitrogen by inserting a gas dispersion tube beneath the surface of the water and bubbling nitrogen through the vessel contents for at least 15 minutes. 40 grams of sodium pyrophosphate, ($Na_4P_2O_7.10H_2O$) was added, stirred until dissolved; and then stirred for an additional fifteen minutes. 800 mg. of stannous chloride ($SnCl_2.2H_2O$) was then added, stirred until dissolved, and stirred for an additional ten minutes. Sufficient hydrochloric acid solution, 1N HCl was added to adjust the pH to 6.3 – 6.5. Then 200 mg. ascorbic acid was added ($C_6H_8O_6$) and stirred until dissolved. The pH was adjusted to 6.1 by addition of hydrochloric acid solution. Water for injection was added to bring the volume to about 1950 ml. The pH was adjusted to 6.0 with the hydrochloric acid solution. The gas dispersion tube was removed and sufficient water for injection was added to bring the volume to 2,000 ml. It was then stirred for two minutes to assure thorough mixing.

B. Filtration

The solution was filtered through a 0.22 μm membrane filter immediately after preparation. The first 100 ml. of filtrate was discarded and the remainder collected in an appropriate size sterile pyrogenfree collection vessel.

C. Dispensing 1.0 ± .05 ml. was dispersed into sterile, pyrogenfree, U.S.P. Type I glass vials and partially stoppered. The partially stoppered vials were placed in lyophilizing trays, and lyophilized.

EXAMPLE 2

The procedure of Example 1 was repeated with the exception that 10 grams of potassium per chlorate was added after the stannous chloride was dissolved.

EXAMPLE 3

The following tests to evaluate the quality of the compositions of this invention were performed:

Radiochemical Purity

1. Labeling efficiency and stability. Reconstitute 2 vials of stannous pyrophosphate by adding 5 ml. of sodium pertechnetate solution (50 – 100 mCi). Shake the samples to assure complete solution. Five minutes, 6 hours, and 24 hours after labeling apply a single drop of sample about 2.3 – 3.0 cm. from the end of a 2.5 × 30 cm. strip of Whatman 3mm chromatography paper. Instantly place the strips in the solvent tanks and develop by the ascending movement of Methanol : 5.8% Ammonium Hydroxide (85:15). After the solvent has migrated at least 15 cm., remove the strips from the solvent chamber and air dry. Determine the distribution of radioactivity on each strip by scanning on a suitable collimated radiochromatogram strip scanner. If the main peak is observed at the origin, divide the strip into 2 segments;

Segment 1. Origin to RF = 0.25
Segment 2. Rf 0.25 to solvent front

The strip segments are folded to about the same size and counted at the 99 mTc settings of a properly calibrated spectroscaler and the % 99 mTc-stannous pyrophosphate is computed. The initial (5 minutes) determination measures the efficiency with which the sodium pertechnetate is reduced and bound to the pyrophosphate complex. This same procedure, when repeated at 6 hours and again at 24 hours, detects any decomposition which has occurred.

If the conversion of $TcO^-_4$ to Technetated pyrophosphate is complete, nearly 100% of the 99mTc radioactivity remains at the origin. Unconverted $TcO^-_4$ will migrate with the solvent and has an Rf of about 0.6 to 0.7. A composition which displays good labeling and tagged stability properties will have near 100% of the radioactivity remaining at the origin at all time intervals. Appearance of radioactivity at an Rf of 0.6 to 0.7 reflects either poor initial binding of pertechnetate or that decomposition is taking place.

2. Insoluble Impurities.

Reconstitute 2 vials stannous pyrophosphate by adding 5 ml. of sodium pertechnetate solution (50–100 mCi). Shake the vials to assure complete solution. 5 minutes, 6 hours and 24 hours after labeling, apply a single drop of sample 2.5 – 3.0 cm. from the end of a Gelman ITLC - SG chromatography plate (5 × 20 cm.). Immediately transfer the strips to a vertical glass chromatography chamber, and develop by the ascending movement of 0.9% Sodium Chloride for injection. Continue developing until the solvent has migrated at least 15 cm. Remove from the tank and allow to air dry.

Scan the strip in a suitable collimated radiation strip scanner. If the majority of radioactivity on the strip appears at the solvent front, section the strip into two segments:

Segment 1 = Origin to Rf 0.25
Segment 2 = Rf 0.25 to solvent front + 2 cm.

The segments are folded to equal size and counted at the 99 mTc settings of a calibrated spectroscaler and the % of insoluble impurities is computed. Any insoluble forms of technetium which may be present (i.e., hydrated reduced technetium, technetated stannous hydroxide, etc.) will remain at the point of sample application while technetated pyrophosphate and unbound pertechnetate will migrate to the solvent front. Improper manufacturing procedures, introduction of contaminants, or poor quality sources of sodium pertechnetate solutions may result in unacceptable levels of insoluble technetium compounds. Generally, a value of $\geq 5\%$ at the origin is considered to be unacceptable and thought to result in elevated liver deposition.

A sample which shows low or minimal quantities of insoluble technetium compounds initially, and which increases in amount with time is thought to be undergoing decomposition. The significance of this type of sample decomposition is not completely understood, but the insoluble forms of technetium are thought to be actively deposited in the liver.

Bioassay (Mice and Rabbits):

1. Mouse Bioassay.

Reconstitute 2 vials of Stannous Pyrophosphate with 5 ml. of sodium pertechnetate solution (10 – 20 mCi/ml). One to two hours after sample reconstitution, transfer 0.30 ml. of sample into 10 cc. vials containing 5.7 ml. of nitrogen purged 0.9% Sodium Chloride for injection.

Immediately after dilution, inject 3 mice (15 – 25 gm.) with 0.03 ml. of the sample dilution. Determine the body burden of each mouse just after injection using a suitable radiation detection instrument. Compare the mouse body burdens to the radioactivity content of a phantom standard which is prepared by adding 0.030 ml. of the dilution to 20 ml. of water using a precision syringe. The phantom should be prepared in duplicate and placed in vials which approximate the size of the mice. If the mice body burdens are outside the range of 70 – 130% of the phantom standard, discard that mouse and inject another. Record the injection time, mouse body burden and phantom content.

After injection and body burden measurements are completed, cage the mice, allowing them access to water but no food.

Each mouse is sacrificed 2 hours ± 5 minutes after injection by overdose of chloroform anesthesia. Each of the mice is dissected by carefully removing the liver and femur.

The entire liver must be obtained. The entire femur is removed carefully, cleaned of soft tissue, and the distal cartilage and epiphysis removed and separated from the diaphyses. The proximal epiphysis is not removed.

The tissues are placed in labeled counting vials and a 5% counting standard prepared. The 5% standard is prepared by transferring 0.30 ml. of the sample dilution (used for injection) to a 100 ml. of volumetric flask and diluting to the mark. Mix the contents of the flask thoroughly and transfer 0.50 ml. to counting vials. Prepare in duplicate. The counting vials containing the standards should be identical in size and shape to those used to contain the tissues.

Count the tissue samples and standards on a suitably calibrated spectroscaler - NaI crystal. Take care to count all samples using a similar $2\pi$ geometrical position.

Calculate the % of adm. dose for each tissue sample as follows:

$$\% \text{ dose/tissue} = \frac{\text{Phantom Counts} \times \text{Tissue Counts}}{\text{Body Burden Counts} \times 5\% \text{ STD.Counts}} \times 5$$

Compute the average % in femur and average % in liver.

2. Rabbit Bioassay.

Injection Preparation

Reconstitute the sample vials by adding 1 mCi of sodium pertechnetate Tc-99m and diluting to 5 ml. with sodium chloride injection.

Prepare a strontium nitrate Sr-85 sample which has a concentration of approximately 3.5 uCi/ml.

Tc-99m Standard Preparation

Accurately transfer 0.5 ml. of the reconstituted Tc-99m pyrophosphate sample into a 100 ml. volumetric flask. Add sufficient distilled water to bring volume to 100 ml. and mix well. Accurately transfer 2.0 ml. of the Tc-99m standard to a sample vial geometrically identical to the vial used for the tissue sample.

Sr-85 Standard Preparation

Accurately transfer 2.0 ml. of the strontium nitrate Sr-85 sample to a 100 ml. volumetric flask. Add sufficient distilled water to bring volume to 100 ml. and mix well. Accurately transfer 2.0 ml. of the Sr-85 standard to a sample vial geometrically identical to the vial used for the tissue sample.

Procedure a. Inject into the ear vein of a rabbit weighing between 3 - 4 kg. 0.5 ml. (approximately 100 uCi) from the reconstituted sample containing the Tc-99m stannous pyrophosphate and also 2 ml. (approximately 7 uCi) of strontium nitrate Sr-85). After two hours, sacrifice the rabbit with chloroform. Remove the liver. Remove a representative sample of liver (about 2 gm.) place in a pre-weighed sample vial and record the sample weight. Remove one femur, scrape clean of muscle and cartilage. Fracture the femur and remove all the marrow. Continue breaking the femur into small pieces such that each section will fit into three sample vials. Try to distribute the broken femur segments into sample vials. Count all the tissue samples in a spectroscaler well for Tc-99m and Sr-85.

b. The following standard counts are recorded at the same time the tissue counts are made:
A. Counts for the Tc-99m standard at the Tc-99m setting.
B. Counts for the Sr-85 standard at the Sr-85 setting.
C. Counts for the Sr-85 standard at the Tc-99m setting.

c. Calculations of total counts administered:
A. Total Tc-99m counts administered = Tc-99m standard counts (bA) × 50.
B. Total Sr-85 counts administered = Sr-85 standard counts (bB) × 50.
C. Sr-85 contribution factor at the Tc-99m setting = Sr-85 standard counts at Tc-99m (bC) setting divided by Sr-85 standard counts at Sr-85 setting (bB):

b (C)/b (B)

d. Record the sum of all the Tc-99m counts for the femur at the Tc-99m setting. Record the sum of all the Sr-85 counts for the femur at the Sr-85 setting. Calculate the % in femur as follows:

%Tc-99m in femur = (A)

$$\frac{[\text{Tc-99m femur counts} - (\text{Sr-85 femur counts} \times \text{Sr-85 contrib.factor})]}{\text{Total Tc-99m counts administered}} \times 100$$

%Sr-85 in femur = (B)

$$\frac{\text{Sr-85 counts in femur}}{\text{Sr-85 counts administered}} \times 100$$

Tc-99m to Sr-85 ratio in femur = (C)

$$\frac{\%\text{Tc-99m in femur}}{\%\text{Sr-85 in femur}}$$

e. Record the Tc-99m counts for the liver sample. Record the Sr-85 counts for the liver sample. Calculate the % Tc-99m in the liver per gram Percent Tc-99m per gram.

$$\frac{\text{Tc-99m counts for liver} - (\text{Sr-85 counts for liver} \times \text{Sr-85 contrib. factor}) \times 100}{\text{Tc-99m counts administered} \times \text{gm. liver in sample}}$$

Rabbit Scintigrams

A vial of stannous pyrophosphate is reconstituted by addition of 5 ml. of sodium pertechnetate solution. The prepared sample is permitted to age for 3- 4 hours and then 0.2 ml. is injected into the marginal ear vein of a rabbit weighing between 3 - 4 kg. Two hours after injection the rabbits are imaged using a gamma camera. The images are evaluated for bone clarity, presence of liver contribution, and the amount of soft tissue contribution. The liver and soft tissue contributions are given a rating according to the following key.

| | LIVER | |
|---|---|---|
| Excellent | 0 = | none |
| Good | 1 = | perceptible (not objectionable) |
| Fair | 2 = | equal to diaphyses of femur |
| Poor | 3 = | equal to lumbar vertebrae or sternum |
| Unsatifactory | 4 = | equal to epiphysis |
| Unacceptable | 5 = | greater than epiphysis |

| | SOFT TISSUE | |
|---|---|---|
| Excellent | 0 = | none |
| Good | 1 = | perceptible (not objectionable) |
| Fair | 2 = | moderate (bone still clearly defined) |
| Poor | 3 = | objectionable (level in soft tissue is sufficient to distort diaphyses) |
| Unsatisfactory | 4 = | diaphyses and soft tissue indistinguishable. |
| Unacceptable | 5 = | the skeleton and soft tissue are not distinguishable. |

A liver rating of 2 or less and a soft tissue rating of 3 or less indicates that the image has diagnostic utility. However, to obtain scans that are considered to be of a desired quality a liver rating of 1 or less and a soft tissue rating of 2 or less must be achieved.

Results for the three lots (A, B, C) prepared by the procedure of Example 1 are given in Table 1. Results for three lots (A, B, C) prepared by the procedure of Example 2 are given in Table 2. Results for two lots prepared by the procedures of both Examples and stored at 50° C. are given in Table 3. Table 4 gives the results of compositions containing ascorbic acid alone, perchlorate alone and both together. These results are representative of tests made on the compositions of the instant invention containing stannous pyrophosphate and ascorbate and optionally perchlorate.

TABLE 1.

STABILITY AND QUALITY PERFORMANCE DATA

| | | | RADIOCHEMICAL PURITY | | | | | | BIOASSAY | | | Rabbit Scans |
|---|---|---|---|---|---|---|---|---|---|---|---|---|
| | | | MeOH-3MM | | | 0.9% NaCl-ITLC-SG | | | Mouse | | Rabbit | LIVER, |
| Lot No. | Age Test | Appearance | 5 min. | 6 Hr. | 24 Hr. | 5 min. | 6 Hr. | 24 Hr. | % Liver | % Femur | %/Gram (LIVER) | Tc:Sr (FEMUR) | SOFT TISSUE |
| A | 1 wks | Clear Solution | 99.7% | 98.6% | 95.6% | 0.28% | 0.36% | 0.51% | 0.49% | 1.36% | — | — | (0, 0) |
| | 4 wks | " | 99.7 | 97.9 | 97.0 | 0.32 | 0.40 | 0.54 | 0.53 | 1.10 | — | — | (0, 2) |
| | 8 wks | " | 98.9 | 95.8 | 90.1 | 0.57 | 0.75 | 1.61 | 0.54 | 1.31 | — | — | (0, 1) |
| | 12 wks | " | 98.9 | 99.2 | 98.0 | 0.65 | 0.56 | 0.35 | 0.49 | 1.33 | — | — | (0, 0) |
| | 16 wks | " | 99.6 | 96.6 | 96.3 | 0.69 | 0.62 | 0.43 | 0.79 | 1.50 | 0.04% | 0.73 | (0, 0) |

TABLE 1.-continued
STABILITY AND QUALITY PERFORMANCE DATA

| | | | | | | | | | | | | | |
|---|---|---|---|---|---|---|---|---|---|---|---|---|---|
| B | 1 wks | " | 99.9% | 98.2% | 93.2% | 0.46% | 0.60% | 0.78% | 0.80 | 1.75 | — | — | (0, 0+) |
| | 2 wks | " | 99.6 | 98.1 | 94.5 | 0.66 | 0.39 | 0.85 | 0.77 | 1.24 | — | — | (0, 1) |
| | 6 wks | " | 99.5 | 98.1 | 94.0 | 0.39 | 0.47 | 0.90 | 0.66 | 1.57 | — | — | (0, 0) |
| | 10 wks | " | 98.0 | 91.7 | 93.9 | 0.44 | 0.89 | 1.33 | 0.90 | 1.15 | — | — | (0, 0) |
| | 14 wks | " | 98.4 | 97.0 | 91.1 | 0.56 | 1.06 | 1.04 | 0.82 | 2.31 | 0.05 | 0.93 | (0+,0+) |
| C | 1 wks | " | 99.8% | 96.3 | 90.7 | 0.29% | 0.55% | 1.46% | 0.71 | 1.66% | — | — | (0+,0) |
| | 2 wks | " | 99.8% | 98.5 | 96.6 | 0.45 | 0.41 | 0.53 | 0.64 | 1.15 | — | — | (0, 0+) |
| | 6 wks | " | 99.7 | 98.6 | 95.4 | 0.51 | 0.50 | 1.29 | 0.96 | 1.17 | — | — | (0, 1) |
| | 10 wks | " | 99.9 | 98.7 | 97.5 | 0.47 | 0.34 | 0.55 | 0.49 | 1.25 | — | — | (0, 0) |
| | 14 wks | " | 99.7 | 99.5 | 96.5 | 0.31 | 0.86 | 0.87 | 0.83 | 1.68 | 0.03% | 1.04 | (0, 0) |

| LIVER | | SOFT TISSUE | |
|---|---|---|---|
| Excellent | 0 = none | Excellent | 0 = none |
| Good | 1 = perceptible (not objectionable) | Good | 1 = perceptible (not objectionable) |
| Fair | 2 = equal to diaphyses of femur | Fair | 2 = moderate (bone still clearly defined) |
| Poor | 3 = equal to lumbar vertebrae or sternum | Poor | 3 = objectionable (level in soft tissue is sufficient to distort diaphyses) |
| Unsatisfactory | 4 = equal to epiphysis | Unsatisfactory | 4 = diaphyses and soft tissue indistinguishable |
| Unacceptable | 5 = greater than epiphysis | Unacceptable | 5 = the skeleton and soft tissue are not distinguishable |

TABLE 2.
STABILITY AND QUALITY PERFORMANCE DATA

| Lot No. | Age Test | Appearance | RADIOCHEMICAL PURITY | | | | | | BIOASSAY | | | | Rabbit Scans LIVER, SOFT TISSUE |
|---|---|---|---|---|---|---|---|---|---|---|---|---|---|
| | | | MeOH-3MM | | | 0.9% NaCl-ITLC-SG | | | Mouse | | Rabbit | | |
| | | | 5 min. | 6 Hr. | 24 Hr. | 5 min. | 6 Hr. | 24 Hr. | % Liver | % Femur | %/Gram (LIVER) | Tc:Sr (FEMUR) | |
| A | 1 wks | Clear Solution | 99.9 | 98.8 | 95.2 | 0.067 | 0.275 | 0.327 | 0.53 | 1.28 | NT | NT | (0, 0) |
| | 4 wks | " | 99.7 | 98.6 | 98.2 | 1.16 | 0.580 | 0.460 | 0.60 | 1.12 | NT | NT | (0, 1) |
| | 8 wks | " | 99.0 | 97.7 | 93.9 | 0.69 | 1.03 | 1.01 | 0.54 | 1.21 | NT | NT | (0, 0+) |
| | 12 wks | " | 99.8 | 96.8 | 96.9 | 0.36 | 0.75 | 0.64 | 0.49 | 1.06 | NT | NT | (0, 0+) |
| | 16 wks | " | 99.8 | 99.6 | 95.7 | 0.67 | 0.52 | 0.55 | 0.98 | 1.44 | 0.02 | 0.93 | (0, 0) |
| B | 1 wks | " | 99.9 | 96.8 | 90.1 | 0.38 | 0.77 | 1.69 | 0.65 | 1.57 | NT | NT | (0, 1) |
| | 2 wks | " | 99.8 | 97.2 | 94.4 | 0.45 | 0.44 | 0.80 | 0.66 | 1.55 | NT | NT | (0, 0) |
| | 6 wks | " | 99.1 | 96.1 | 92.1 | 0.67 | 0.83 | 1.06 | 0.72 | 1.32 | NT | NT | (0, 1) |
| | 10 wks | " | 99.7 | 96.2 | 95.0 | 0.34 | 0.41 | 1.15 | 0.75 | 1.32 | NT | NT | (0, 0) |
| | 14 wks | " | 99.7 | 98.8 | 92.2 | 0.56 | 0.78 | 1.19 | 0.87 | 1.64 | 0.04 | 1.02 | (0, 0+) |
| C | 1 wks | " | 99.9 | 97.8 | 92.3 | 0.55 | 0.93 | 1.28 | 0.62 | 1.68 | NT | NT | (0, 0) |
| | 2 wks | " | 99.8 | 98.3 | 95.1 | 1.29 | 0.68 | 0.74 | 0.59 | 1.31 | NT | NT | (0, 0+) |
| | 6 wks | " | 99.6 | 97.9 | 92.5 | 0.72 | 0.73 | 1.38 | 0.53 | 1.41 | NT | NT | (0, 0) |
| | 10 wks | " | 99.8 | 97.8 | 96.5 | 0.31 | 0.54 | 0.92 | 0.67 | 1.37 | NT | NT | (0, 0) |
| | 14 wks | " | 99.9 | 99.2 | 94.5 | 0.19 | 0.73 | 0.85 | 0.79 | 1.35 | 0.05 | 0.90 | (0, 0) |

| LIVER | | SOFT TISSUE | |
|---|---|---|---|
| Excellent | 0 = none | Excellent | 0 = none |
| Good | 1 = perceptible (not objectionable) | Good | 1 = perceptible (not objectionable) |
| Fair | 2 = equal to diaphyses of femur | Fair | 2 = moderate (bone still clearly defined) |
| Poor | 3 = equal to lumbar vertebrae or sternum | Poor | 3 = objectionable (level in soft tissue is sufficient to distort diaphyses) |
| Unsatisfactory | 4 = equal to epiphysis | Unsatisfactory | 4 = diaphyses and soft tissue indistinguishable |
| Unacceptable | 5 = greater than epiphysis | Unacceptable | 5 = the skeleton and soft tissue are not distinguishable |

TABLE 3.

| Lot No. | Ingredients | pH | Storage | Product Age | RADIOCHEMICAL PURITY MeOH-3MM | | | 0.9% NaCl-ITLC-SG | | | BIOASSAY Mouse | | | | | Rabbit Scans | |
|---|---|---|---|---|---|---|---|---|---|---|---|---|---|---|---|---|---|
| | | | | | Initial | 6 Hr. | 24 Hr. | Initial | 6 Hr. | 24 Hr. | % Liver | % GI | % Kidney | % Muscle | % Femur | LIVER | SOFT TISSUE |
| A | Ascorbic Acid | 6.0 | 50° C. | 2 weeks | 99.4 | 94.0 | 88.2 | 3.8 | 1.2 | .6 | 2.3 | 5.0 | 1.6 | 3.9 | 1.1 | (0, 0) | |
| A | " | 6.5 | " | " | 92.4 | 91.4 | 81.9 | 3.1 | 1.2 | .7 | 3.8 | 4.8 | 2.2 | 5.5 | .8 | (0, 0) | |
| A | " | 6.0 | " | 4 weeks | 98.7 | 80.8 | 2.6 | 6.1 | 10.9 | 7.5 | 2.8 | 3.5 | .7 | 2.6 | 1.5 | (2, 2+) | |
| A | " | 6.5 | " | " | 98.2 | 92.2 | 39.1 | 4.4 | 8.6 | 7.4 | 2.1 | 2.9 | .6 | 4.3 | 1.4 | (2+, 1) | |
| B | Ascorbic Acid Perchlorate | 6.0 | " | 2 weeks | 99.3 | 81.9 | 73.1 | 3.7 | .7 | .5 | NT | NT | NT | NT | NT | NT | |
| B | " | 6.5 | " | " | 99.0 | 90.3 | 78.5 | 4.7 | 1.8 | .8 | 3.2 | 5.3 | 2.6 | 3.2 | .5 | (1, 0) | |
| B | " | 6.0 | " | 4 weeks | 100 | 98.5 | 96.2 | 1.3 | 2.3 | 2.5 | .8 | 1.9 | .5 | 4.0 | .8 | (0, 0+) | |
| B | " | 6.5 | " | " | 99.5 | 95.7 | 76.8 | 3.5 | 5.8 | 10.5 | 1.3 | 4.6 | .6 | 3.1 | 1.7 | (1, 1+) | |

LIVER
0 = None
1 = Perceptible (not objectionable)
2 = Equal to diaphyses of femur
3 = Equal to lumbar vertebrae or sternum
4 = Equal to epiphysis
5 = Greater than epiphysis Excellent
Good
Fair
Poor
Unsatisfactory
Unacceptable

SOFT TISSUE
0 = None
1 = Perceptible (not objectionable)
2 = Moderate (bone still clearly defined)
3 = Objectionable (level in soft tissue is sufficient to distort diaphyses)
4 = Diaphyses and soft tissue indistinguishable
5 = The skeleton and soft tissue are not distinguishable NT = Not taken

TABLE 4

| Lot No. | Ascorbic Acid | KClO4 | Age | pH | RADIOCHEMICAL PURITY | | | | | | BIOASSAY Mouse | | | | |
|---|---|---|---|---|---|---|---|---|---|---|---|---|---|---|---|
| | | | | | MeOH/NH4-OH-3MM | | | 9% NaCl-SG | | | % Liver | % GI | % Kidney | % Muscle | % Femur |
| | | | | | Initial | 6 Hr. | 24 Hr. | Initial | 6 Hr. | 24 Hr. | | | | | |
| A 5GO | — | — | ~3 Day | 6 | 97.3 | 82.6 | 49.7 | 3.1 | 2.7 | 8.1 | 1.6 | 2.1 | 5.1 | .7 | .97 |
| A 5GO | — | — | ~3 Day | 7 | 98.6 | 87.0 | 53.7 | 2.3 | 2.3 | 7.0 | 2.2 | 2.6 | 5.3 | .3 | .89 |
| B 5IV | .1 mg. | — | 2 Day | 6 | 99.8 | 99.5 | 98.5 | 1.0 | .5 | 1.1 | .6 | 1.6 | .6 | NT | 1.0 |
| C 5IB | — | 5 mg. | 14 Day | 6 | 99.7 | 88.7 | 13.7 | NT | 4.7 | 3.1 | NT | NT | NT | NT | NT |
| D 5IB | .1 mg | 5 mg. | 14 Day | 6 | 100 | 99.6 | 99.6 | | .2 | .4 | NT | NT | NT | NT | NT |
| D 5IB | .1 mg. | 5 mg. | 14 Day | 6 | 99.2 | 98.9 | 88.3 | .6 | .8 | 7.4 | .5 | 1.8 | .5 | 2.5 | 1.2 |

A- 20 mg. Na4P2O7 . 10H2O 0.4 mg. SnCl2 . 2H2O
B- 20 mg. Na4P2O7 . 10H2O 0.4 mg. SnCl2 . 2H2O .1 mg. Ascorbic Acid
C- 20 mg. Na4P2O7 . 10H2O 0.4 mg. SnCl2 . 2H2O 5 mg. KClO4
D- 20 mg. Na4P2O7 . 10H2O 0.4 mg. SnCl2 . 2H2O .1 mg. Ascorbic Acid 5 mg. KClO4
NT = Not taken As various changes could be made in the above methods and products without departing from the scope of the invention, it is intended that all matter contained in the above description shall be interpreted as illustrative. It is to be understood therefore that the invention is not limited except as defined by the appended claims.

What is claimed is:

1. An improved composition for skeletal imaging comprising,
   A. divalent tin
   B. technetium-99m
   C. pyrophosphate, and
   D. sufficient ascorbate to reduce (1) the oxidation of $Sn^{+2}$ to $Sn^{+4}$ during extended storage and (2) reoxidation of reduced technetium and the formation of technetium labeled impurities.

2. A composition according to claim 1 additionally containing perchlorate.

3. An improved lyophilized composition for use in preparing bone scanning agents comprising,
   A. divalent tin
   B. pyrophosphate, and
   C. sufficient ascorbate to reduce (1) the oxidation of $Sn^{+2}$ to $Sn^{+4}$ during extended storage and (2) reoxidation of reduced technetium and the formation of technetium labeled impurities.

4. A composition according to claim 3 additionally containing perchlorate.

5. In a method for bone imaging wherein a bone imaging agent is injected and thereafter a scan made, the improvement comprising using as the bone imaging agent the composition of claim 1.

6. In a method for bone imaging wherein a bone imaging agent is injected and thereafter a scan made, the improvement comprising using as the bone imaging agent the composition of claim 2.

7. A lyophilized composition according to claim 3, wherein the divalent tin and pyrophosphate are present in an amount such that the molar ratio of $Sn/P_2O_7$ is in the range of about 0.010/1.0 to about 0.58/1.0 and the ascorbate is present in an amount of from about .1mg to 2.5mg per mg of divalent tin.

8. A lyophilized composition according to claim 7 wherein the divalent tin and pyrophosphate are present in an amount such that the molar ratio of $Sn/P_2O_7$ is in the range of about 0.02/1.0 to about 0.06/1.0 and the ascorbate is present in an amount of from about 0.21mg to about 1.2mg per mg of divalent tin.

9. An improved lyophilized composition for use in preparing bone scanning agents consisting essentially of stannous chloride, sodium pyrophosphate and ascorbaic acid, the molar ratio of $Sn/P_2O_7$ being in the range of about 0.02/1 to about 0.06/1 and the ascorbic acid being present in an amount to provide about .21mg to about 1.2mg of ascorbate per mg of divalent tin.

10. An improved composition for skeletal imaging comprising a sterile aqueous solution containing divalent tin, technetium 99m, pyrophosphate and ascorbate, the divalent tin and pyrophosphate being present in an amount such that the molar ratio of $Sn/P_2O_7$ is in the range of about 0.010/1 to about 0.58/1, the technetium 99m being present in an amount such that the ratio of $P_2O_7$/technetium 99m is in the range of about 0.012mg/mCi to about 4mg/mCi and the ascorbate being present in an amount of about 0.1mg to about 2.5mg per mg of divalent tin.

11. A composition according to claim 10 wherein the divalent tin and pyrophosphate are present in an amount such that the molar ratio of $Sn/P_2O_7$ is in the range of about 0.02/1 to about 0.06/1 and the technetium 99m is present such that the ratio of $P_2O_7$/technetium 99m is in the range of about 0.03mg/mCi to about 1.2mg/mCi and the ascorbate is present in an amount of about 0.21mg to about 1.2mg per mg of divalent tin.

12. An improved composition for skeletal imaging comprising a sterile aqueous solution consisting essentially of stannous chloride, technetium 99m, sodium pyrophosphate and ascorbic acid, the divalent tin and sodium pyrophosphate being present in an amount such that the molar ratio of $Sn/P_2O_7$ is in the range of about 0.02/1 to about 0.06/1, the technetium 99m is present such that the ratio of $P_2O_7$/technetium 99m is in the range of about 0.03mg/mCi to about 1.2mg/mCi and the ascorbic acid is present in an amount to provide from about 0.21 mg to about 1.2 mg of ascorbate per mg of divalent tin.

13. In a method for bone imaging wherein a bone imaging agent is injected and thereafter a scan made, the improvement comprising using as the bone imaging agent the composition of claim 10.

14. In a method for bone imaging wherein a bone imaging agent is injected and thereafter a scan made, the improvement comprising using as the bone imaging agent the composition of claim 12.

15. A composition according to claim 8 additionally containing perchlorate in an amount of about 20 mg to 30 mg per mg of divalent tin.

16. A composition according to claim 11 additionally containing perchlorate in an amount of about 20 mg to 30 mg per mg of divalent tin.

* * * * *